United States Patent
Faber et al.

(10) Patent No.: US 7,034,178 B2
(45) Date of Patent: Apr. 25, 2006

(54) PROCESS FOR THE PRODUCTION OF 3-PHENYLISOSERINE

(75) Inventors: Wijnand Faber, HG Groningen (NL); Jan Koek, BK Sauwerd (NL); Jörg Senn-Bilfinger, Constance (DE); Ton Vries, JM Groningen (NL)

(73) Assignee: Altana Pharma AG, Constance (DE)

( * ) Notice: Subject to any disclaimer, the term of this patent is extended or adjusted under 35 U.S.C. 154(b) by 0 days.

(21) Appl. No.: 10/482,483

(22) PCT Filed: Jun. 27, 2002

(86) PCT No.: PCT/EP02/07092

§ 371 (c)(1), (2), (4) Date: Dec. 31, 2003

(87) PCT Pub. No.: WO03/003804

PCT Pub. Date: Jan. 16, 2003

(65) Prior Publication Data

US 2004/0176460 A1    Sep. 9, 2004

(30) Foreign Application Priority Data

Jul. 3, 2001  (EP) .................................. 01116083

(51) Int. Cl.
*C07C 229/00*   (2006.01)
*C07B 55/00*   (2006.01)

(52) U.S. Cl. .................. 560/39; 562/401; 562/402; 562/444

(58) Field of Classification Search .................. 560/39; 562/401, 402, 444
See application file for complete search history.

(56) References Cited

U.S. PATENT DOCUMENTS 6,025,516 A    2/2000   Ramaswamy et al.

OTHER PUBLICATIONS

XP-002140516; Harada, Kaoru, *Optical Resolution and Absolute Configuration of trans-β- Phenylglycidic Acid*, J. Org. Chem., vol. 31, pp. 1407-1410 (1966).
XP-002183959; Yu, et al., *Synthesis of (2S, 3R) isomer of taxol side chain*, Chemical Abstracts, vol. 133, No. 1, p. 599 (2000).
XP-002183960; Liebigs, Justus, Beilstein Registry No. 2938805, Reaction 6 of 8.

*Primary Examiner*—Paul A. Zucker
(74) *Attorney, Agent, or Firm*—Nath & Associates PLLC; Joshua B. Goldberg; Sheldon M. McGee

(57) ABSTRACT

This invention is drawn to a process for the production of (R,R)-phenylisoserine or a 1–4C-alkyl ester thereof.

5 Claims, No Drawings

PROCESS FOR THE PRODUCTION OF 3-PHENYLISOSERINE

TECHNICAL FIELD

The invention relates to a process for the production of 3-phenylisosedne and its derivatives in high optical purity. 3-Phenylisoserine is a valuable intermediate in the production of pharmaceuticals.

PRIOR ART

Known processes for the production of 3-phenylisoserine and its derivatives in high optical purity are not suited for the production of these compounds on an industrial scale.

SUMMARY OF THE INVENTION

It has been found, surprisingly, that the process described in more detail below is suited to produce 3-phenylisoserine and its derivatives in high optical purity on an Industrial scale.

The process according to the invention includes mainly two steps: (a) The production of racemic 3-phenylisoserine or a derivative thereof and (b) its separation into the enantiomers. The inventive process is contained in—and can be summarised exemplary by—the following reaction scheme:

DETAILED DESCRIPTION OF THE INVENTION

Subject matter of the invention Is a process for the production of (R, R)-3-phenylisoserine including its 1–4C-alkyl esters which comprises reacting a 3-phenylglycidic acid salt with ammonia to yield the salt of racemic 3-phenylisoserine, converting the salt of racemic 3-phenylisoserine to racemic 3-phenylisoserine 1–4C-alkyl ester and separating the (R, R)-3-phenylisoserine 1–4C-alkyl ester from the racemate by reacting the latter with L-(+)-tartaric acid and working the salt obtained for (R, R)-3-phenyllsoserine 1–4C-alkyl ester.

Likewise, subject matter of the invention is a process for the production of (S, S)-3-phenylisoserine including its 1–4C-alkyl esters which comprises the above reaction steps but using D-(–)-tartaric acid instead of L-(+)-tartaric acid.

As possible salts of the 3-phenylglycidic acid, alkaline-earth metal salts and in particular alkali metal salts have to be mentioned, the potassium and in particular the sodium salt being preferred.

The reaction of the 3-phenylglycidic acid salt with ammonia is carried out preferably in a protic solvent, in particular in water, with an ammonia concentration of about 15 to 33%, preferably with an ammonia concentration of about 20

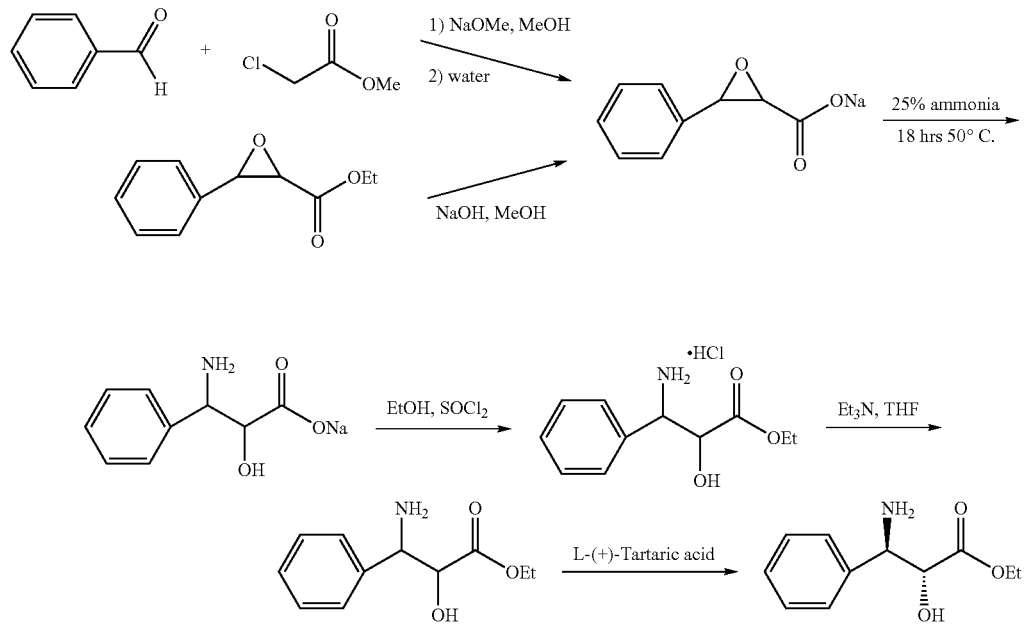

The reaction scheme shall serve as a brief description of the invention without restricting it to the details given eg on the reaction arrows. In the scheme, it is understood that the phenyl ring and the carboxylic group attached to the oxlrane ring are in trans position to each other. In the last formula of the scheme, (R, R)-3-phenylisoserine ethyl ester is shown as reaction product when using L-(+)-tartaric acid as optical resolution agent. Likewise, D(–)tartaric acid can be used in order to obtain (S, S)-3-phenylisoserine ethyl ester in high optical purity.

to 30%, in particular with an ammonia concentration of about 25%, at a temperature between 25 to 75° C., preferably at a temperature between 35 and 65° C., in particular at a temperature between 45 and 55° C. Under the noted conditions, the reaction leads surprisingly mainly to the desired product.

The esterification can be carried out according to known processes, e.g. with thionyl chloride or with hydrogen chloride and the 1–4C-alkyl alcohol the ester of which is desired. The reaction is carried out under conditions as they are known to the expert, for example by using the 1–4C-alkyl alcohol as the solvent and by adding thionyl chloride dropwise at temperatures of <10° C. or by passing hydrogen chloride gas through the solution.

The reaction of the L-(+)-tartaric acid in an appropriate solvent, in particular in the absolute 1–4C-alkyl alcohol corresponding to the racemic 3-phenylisoserine 1–4C-alkyl ester, leads to the tartrate of the racemic 3-phenylisoserine 1–4C-alkyl ester, the (R, R)-form of which surprisingly crystallises in high optical purity. The (R, R)-3-phenylisoserine and its derivatives (like esters, salts, amides etc.) can thus be obtained simply and in an optical purity which up to now was not achievable on an industrial scale.

The following examples serve to illustrate the invention further without restricting it. The abbreviation min stands for minute(s), h for hour(s), ee for enantiomeric excess, m.p. for melting point and RT for room temperature.

EXAMPLES

1. Sodium-3-phenylglycidate
a) 122.6 g (5.33 mol) of sodium are added in portions to 2620 mL of methanol. The sodium methoxide solution is then cooled below 0° C. and a mixture of 250 ml (2.47 mol) of benzaldehyde and 233 ml (2.66 mol) of chloroacetic add methyl ester are added drop by drop, while temperature is kept below 0° C. After addition, the reaction mixture is stirred for 30 minutes at 0° C. and then for 2 h without cooling thus allowing the temperature to rise to RT. The precipitated sodium chloride is filtered off and discarded. To the mother liquor 49.0 ml (2.72 mol) of water are added drop by drop and the mixture is stirred overnight. The product is filtered off, rinsed with some methanol and dried in vacuo. 416 g (2.23 mol; 90%) of the title compound are obtained as white solid of m.p. >275° C. (decomposition).
b) Alternatively, 382.4 g (9.57 mol) of sodium hydroxide are added in portions to a slurry of 2000 g (9.57 mol) of commercial available ethyl-3-phenylglycidate (92% pure) in 12 L of methanol, while the temperature is kept below 30° C. The mixture is stirred for 2 h. The obtained precipitate is collected and rinsed with 2 L of methanol and dried on air to give 1523 g (8.18 mol; 85%) of the title compound as white solid of m.p. >275° C. (decomposition).

2. 3-Phenylisoserine (rac.) sodium salt
1000 g (5.37 mol) of sodium-3-phenylglycidate are stirred in 10 L of 25% ammonia (aq.) for 18 h at 50° C. The solvent is removed under reduced pressure and the resulting slurry is co-evaporated three times with toluene to remove the last traces of water. 1036 g (5.1 mol; 95%) of the title compound are obtained as white solid.

3. 3-Phenylisoserine (rac.) ethyl ester
a) 1036 g (5.1 mol) of 3-phenylisoserine (rac.) sodium salt are stirred in 6000 ml of absolute ethanol. 1047 ml of thionyl chloride are added drop by drop while keeping the temperature below 20° C. The mixture is refluxed for 4 h and stirred overnight while the temperature is allowed to cool to RT. The volatiles are removed in vacuo and the resulting slurry is co-evaporated with tetrahydrofuran. The obtained hydrochloride of the title compound (white solid) is stirred in 8560 ml of tetrahydrofuran (suspension) and 2460 ml of triethylamine are added drop by drop. The suspension is stirred for further 5 h. The triethylamine hydrochloride is filtered off, washed with tetrahydrofuran and discarded. The combined solutions are concentrated in vacuo. 951 g (4.54 mol; 94.7%) of the title compound are obtained as light yellow oil.
b) Alternatively, the title compound is obtained as follows: 50 g (0.25 mol) of 3-phenylisoserine sodium salt are suspended in 500 ml of absolute ethanol. HCl gas is passed through the suspension, which turns into milk white solution in an exothermic reaction. The HCl gas stream is stopped and the reaction mixture is refluxed for 3 hours. After cooling the reaction mixture to room temperature, the excess of HCl is stripped off under vacuum. The ethanol and water is evaporated and co-evaporated from the residue after addition of 100 ml of THF. The obtained residue is suspended in 450 ml of THF, and 125 ml (91 g, 0.90 mol) of triethylamine are added dropwise to the suspension. The reaction mixture is left overnight and filtered over a büchner funnel. Finally the filtrate is evaporated and 48.1 g (96.9%) of yellow oil is obtained which slowly crystallises.

4. (R, R)-3-Phenylisoserine ethyl ester
951.4 g (4.54 mol) of 3-phenylisoserine (rac.) ethyl ester are dissolved in 8020 ml of absolute ethanol and heated at 50° C. 681.4 g (4.54 mol) of L-(+)-tartaric acid are added and a clear solution is obtained. The mixture is heated with stirring under reflux. Before reflux temperature is reached, crystallisation of the salt starts. The mixture is allowed to cool to RT while stirring for 10 h and is then cooled to 10° C. The precipitate is filtered off, rinsed with 2 L of absolute ethanol and dried to yield 38.3% of the title compound with ee of 84.8%. After recrystallisation of the salt in 9780 ml of absolute ethanol and 978 ml of water, 438 g (1.22 mol; 26.8%) of the tartrate of the title compound with ee of 98.6% and m.p. 162.0–162.3° C. are obtained.—844 g (2.35 mol) of the salt obtained are stirred in 5 L of ethyl acetate. 430 mL of 25% aqueous ammonia solution (6.3 mol) are added in the course of 5 minutes. The mixture is stirred for 1 h. After stopping the stirring, the new precipitate formed (diammonium tartrate) is allowed to deposit. The ethyl acetate layer is decanted. The ammonium salt is washed and decanted twice with each time 800 mL of ethyl acetate. The three ethyl acetate layers are combined and evaporated. 485 g (2.32 mol, 99%) of the title compound of m.p. 92,1–94,1° C. are obtained as white solid.

Optical rotation: $[\alpha]_D^{20}$=−14.8° (c=1, ethanol).

The invention claimed is:

1. A process for the production of (R,R)-3-phenylisoserine or a 1–4C-alkyl esters thereof, which comprises:
   a. reacting a 3-phenylglycidic acid salt with ammonia to yield a salt of racemic 3-phenylisoserine,
   b. converting the salt of racemic 3-phenylisoserine to racemic 3-phenylisoserine 1–4C-alkyl ester, and
   c. separating the (R,R)-3-phenylisoserine 1–4C-alkyl ester from the racemate by reacting the latter with L-(+)-tartaric acid.

2. A process for the separation of (R,R)-3-phenylisoserine 1–4C-alkyl ester from a racemic mixture of 3-phenylisoserine 1–4C-alkyl ester, which comprises reacting a racemic mixture of 3-phenylisoserine 1–4C-alkyl ester with L-(+)-tartaric acid.

3. A process for the separation of (S,S)-3-phenylisoserine 1–4C-alkyl ester from a racemic mixture of 3-phenylisoserine 1–4C-alkyl ester, which comprises reacting a racemic mixture of 3-phenylisoserine 1–4C-alkyl ester with D-(−)-tartaric acid.

4. A process for the separation of (R,R)-3-phenylisoserine or a salt or a 1–4C-alkyl ester thereof from a racemic mixture of 3-phenylisoserine or salts or 1–4C-alkyl esters thereof, which comprises reacting a racemic mixture of 3-phenylisoserine or a salt or a 1–4C-alkyl ester thereof with L-(+)-tartaric acid.

5. A process for the separation of (S,S)-3-phenylisoserine or a salt or a 1–4C-alkyl ester thereof from a racemic mixture of 3-phenylisoserine or salts or 1–4C-alkyl esters thereof, which comprises reacting a racemic mixture of 3-phenylisoserine or a salt or a 1–4C-alkyl ester thereof with D-(−)-tartaric acid.

* * * * *

UNITED STATES PATENT AND TRADEMARK OFFICE
CERTIFICATE OF CORRECTION

PATENT NO. : 7,034,178 B2 Page 1 of 1
APPLICATION NO. : 10/482483
DATED : April 25, 2006
INVENTOR(S) : Faber et al.

It is certified that error appears in the above-identified patent and that said Letters Patent is hereby corrected as shown below:

Claim 1, Column 4, Line 51, Please delete "esters" and replace with -- ester --

Signed and Sealed this

Twenty-fifth Day of July, 2006

JON W. DUDAS
*Director of the United States Patent and Trademark Office*